(12) United States Patent
Krishnan et al.

(10) Patent No.: US 8,521,246 B2
(45) Date of Patent: Aug. 27, 2013

(54) CABLE CROSS TALK SUPPRESSION

(75) Inventors: Kalpathy Krishnan, Boulder, CO (US);
Tom Wilmering, Westminster, CO (US);
Thomas Geske, Erie, CO (US)

(73) Assignee: Covidien LP, Mansfield, MA (US)

( * ) Notice: Subject to any disclaimer, the term of this patent is extended or adjusted under 35 U.S.C. 154(b) by 390 days.

(21) Appl. No.: 12/845,817

(22) Filed: Jul. 29, 2010

(65) Prior Publication Data

US 2012/0029330 A1      Feb. 2, 2012

(51) Int. Cl.
*A61B 5/00*       (2006.01)

(52) U.S. Cl.
USPC .......................................................... 600/323

(58) Field of Classification Search
USPC ................................................ 600/323–324
See application file for complete search history.

(56) References Cited

U.S. PATENT DOCUMENTS

| | | | |
|---|---|---|---|
| 4,819,752 A * | 4/1989 | Zelin ............................ | 600/322 |
| 4,869,254 A | 9/1989 | Stone et al. | |
| 5,078,136 A | 1/1992 | Stone et al. | |
| 5,323,776 A * | 6/1994 | Blakeley et al. .............. | 600/324 |
| 6,259,573 B1 * | 7/2001 | Tsuwako et al. ................ | 360/46 |
| 6,405,069 B1 | 6/2002 | Oraevsky et al. | |
| 6,678,543 B2 * | 1/2004 | Diab et al. ..................... | 600/323 |
| 6,963,767 B2 * | 11/2005 | Rantala et al. ................ | 600/336 |
| 7,035,679 B2 | 4/2006 | Addison et al. | |
| 2005/0070774 A1 | 3/2005 | Addison et al. | |
| 2007/0004977 A1 | 1/2007 | Norris | |
| 2009/0247846 A1 * | 10/2009 | Rantala ......................... | 600/323 |
| 2011/0209915 A1 * | 9/2011 | Telfort et al. ................. | 174/71 R |

FOREIGN PATENT DOCUMENTS

| | | |
|---|---|---|
| EP | 1491135 | 12/2004 |
| JP | 3170866 | 7/1991 |
| JP | 3238813 | 10/1991 |
| JP | 4332536 | 11/1992 |
| JP | 7124138 | 5/1995 |
| JP | 7136150 | 5/1995 |
| JP | 2003194714 | 7/2003 |
| JP | 2003210438 | 7/2003 |
| JP | 2004008572 | 1/2004 |
| JP | 2004113353 | 4/2004 |
| JP | 2004194908 | 7/2004 |
| JP | 2004248819 | 9/2004 |
| JP | 2004290545 | 10/2004 |

(Continued)

OTHER PUBLICATIONS

Leahy, Martin J., et al.; "Sensor Validation in Biomedical Applications," *IFAC Modelling and Control in Biomedical Systems*, Warwick, UK; pp. 221-226 (1997).

(Continued)

*Primary Examiner* — Clayton E Laballe
*Assistant Examiner* — Leon W Rhodes, Jr.

(57) ABSTRACT

Systems, methods, and devices are provided for suppressing cross-talk noise due to capacitive and/or inductive coupling in a medical sensor signal. For example, an embodiment of a patient monitor may include driving circuitry, an amplifier, and transient current discharge circuitry. When the driving circuitry drives an emitter to emit light into a patient, a detector may detect a portion of the light that passes through the patient, generating a detector signal. Cross-talk between the emitter driving signals and the detector signal may generate interference in the form of a transient current in the detector signal. Before the amplifier receives the detector signal, transient current discharge circuitry may discharge the transient current.

20 Claims, 6 Drawing Sheets

(56) References Cited

FOREIGN PATENT DOCUMENTS

| WO | WO 9101678 | 2/1991 |
|---|---|---|
| WO | WO 9309711 | 5/1993 |
| WO | WO 9843071 | 10/1998 |
| WO | WO 9932030 | 7/1999 |
| WO | WO 0021438 | 4/2000 |

OTHER PUBLICATIONS

Barreto, Armando B., et al.; "Adaptive LMS Delay Measurement in dual Blood Volume Pulse Signals for Non-Invasive Monitoring," *IEEE*, pp. 117-120 (1997).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Kaestle, S.; "Determining Artefact Sensitivity of New Pulse Oximeters in Laboratory Using Signals Obtained from Patient," *Biomedizinische Technik*, vol. 45 (2000).

Cysewska-Sobusaik, Anna; "Metrological Problems With noninvasive Transillumination of Living Tissues," *Proceedings of SPIE*, vol. 4515, pp. 15-24 (2001).

Belal, Suliman Yousef, et al.; "A fuzzy system for detecting distorted plethysmogram pulses in neonates and paediatric patients," *Physiol. Meas.*, vol. 22, pp. 397-412 (2001).

Maletras, Francois-Xavier, et al.; "Construction and calibration of a new design of Fiber Optic Respiratory Plethysmograph (FORP)," Optomechanical Design and Engineering, *Proceedings of SPIE*, vol. 4444, pp. 285-293 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Chan, K.W., et al.; "17.3: Adaptive Reduction of Motion Artifact from Photoplethysmographic Recordings using a Variable Step-Size LMS Filter," *IEEE*, pp. 1343-1346 (2002).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

A. Johansson; "Neural network for photoplethysmographic respiratory rate monitoring," *Medical & Biological Engineering & Computing*, vol. 41, pp. 242-248 (2003).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

J. Huang, et al.; "Low Power Motion Tolerant Pulse Oximetry," *Abstracts*, A7, p. S103. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Odagiri, Y.; "Pulse Wave Measuring Device," *Micromechatronics*, vol. 42, No. 3, pp. 6-11 (undated) (Article in Japanese—contains English summary of article).

Neumann, R., et al.; "Fourier Artifact suppression Technology Provides Reliable $SpO_2$," *Abstracts*, A11, p. S105. (undated).

* cited by examiner

CABLE CROSS TALK SUPPRESSION

BACKGROUND

The present disclosure relates generally to medical monitoring systems and, more particularly, to non-invasive medical monitoring systems employing optical sensors.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A wide variety of devices have been developed for non-invasively monitoring physiological characteristics of patients. For example, a pulse oximetry sensor system may detect various patient blood flow characteristics, such as the blood-oxygen saturation of hemoglobin in arterial blood, the volume of individual blood pulsations supplying the tissue, and/or the rate of blood pulsations corresponding to each heart beat of a patient. To determine these physiological characteristics, light may be emitted into patient tissue, where the light may be scattered and/or absorbed in a manner dependent on such physiological characteristics.

Non-invasive medical sensor systems may include a medical sensor and an electronic patient monitor. The monitor may send driving signals to an emitter in the sensor, causing the sensor to emit light into pulsatile patient tissue. A detector in the medical sensor may detect the light after it has passed through the patient tissue, generating an electrical current proportional to the amount of detected light. This electrical current, referred to as a photocurrent, may be received by the patient monitor and converted into a voltage signal using a current-to-voltage (I-V) converter. The resulting voltage signal subsequently may be analyzed to determine certain physiological characteristics of the patient tissue.

When the I-V converter transforms the photocurrent from the photodetector to a voltage signal, thermal noise, also known as Johnson noise, may arise. The Johnson noise may be proportional to the square root of a transimpedance employed by the I-V converter, while the signal gain of the I-V converter may be directly proportional to the transimpedance. As a result, the higher the transimpedance, the higher the signal-to-noise ratio (SNR) of the I-V converter based on Johnson noise (e.g., when the transimpedance increases by a factor of ten, the SNR improves by a factor of $\sqrt{10}$). On the other hand, the higher gain brought about by the higher transimpedance may cause the I-V converter to amplify the photocurrent beyond a signal saturation region of the I-V converter, which may produce a distorted output voltage signal.

The photocurrent and the emitter driving signals may share a cable between the medical sensor and the patient monitor. Despite cable shielding, capacitive and/or inductive coupling may occur between the emitter driving signals and the photocurrent. Thus, when the emitter driving signals rapidly change to turn the emitter on or off, a transient current may arise in the photocurrent. This transient current may discharge slowly as the I-V converter transforms the photocurrent to an output voltage signal. The higher the transimpedance of the I-V converter, the slower the I-V converter may discharge the transient current. Since the transient current of the photocurrent represents noise, the voltage signal that is obtained while the transient current is discharging may be noisy and therefore discarded. Accordingly, patient monitors may employ relatively low transimpedances to ensure the transient current discharges quickly enough to obtain a useful output voltage signal. However, a lower transimpedance may also provide a lower sensitivity.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Embodiments of the present disclosure relate to systems, methods, and devices for suppressing cross-talk noise due to capacitive and/or inductive coupling in a medical sensor signal. For example, an embodiment of a patient monitor may include driving circuitry, an amplifier, and transient current discharge circuitry. When the driving circuitry drives an emitter to emit light into a patient, a detector may detect a portion of the light that passes through the patient, generating a detector signal. Cross-talk between the emitter driving signals and the detector signal may generate interference in the form of a transient current in the detector signal. Before the amplifier receives the detector signal, the transient current discharge circuitry may discharge the transient current.

BRIEF DESCRIPTION OF THE DRAWINGS

Various aspects of this disclosure may be better understood upon reading the following detailed description and upon reference to the drawings in which.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to medical sensor systems for non-invasively monitoring physiological patient characteristics. These systems may involve emitting light through patient tissue using an emitter and detecting an amount of light scattered by the patient tissue using a photodetector. The photodetector may generate a photocurrent, which may be converter to an output voltage signal for use by an electronic patient monitor using a current-to-voltage (I-V) converter in the monitor. Processing circuitry may analyze the output voltage signal to obtain physical parameters of the patient, including the blood-oxygen saturation of hemoglobin arterial blood, the volume of individual blood pulsations supplying the tissue, and/or the rate of blood pulsations corresponding to each heart beat of a patient.

The electronic patient monitor may transmit emitter driving signals across a cable to cause the emitter to emit light into the patient. Rapid changes in the current of the emitter driving signals may cause the emitter to begin or to stop emitting light into the patient, but may also generate interference in the form of a transient current in the photocurrent through capacitive and/or inductive coupling. Rather than slowly discharge the transient current using a transimpedance of the I-V converter, the patient monitor may discharge the transient current to ground when transient current is expected. Discharging the transient current to ground could occur much more rapidly than discharging the transient current using the I-V converter. Indeed, in certain embodiments, the transient current may be discharged to ground over approximately 10 µs or less. Moreover, this discharge time may remain low even if the transimpedance of the I-V converter is increased, which may otherwise increase the transient current discharge time.

Figure 1:
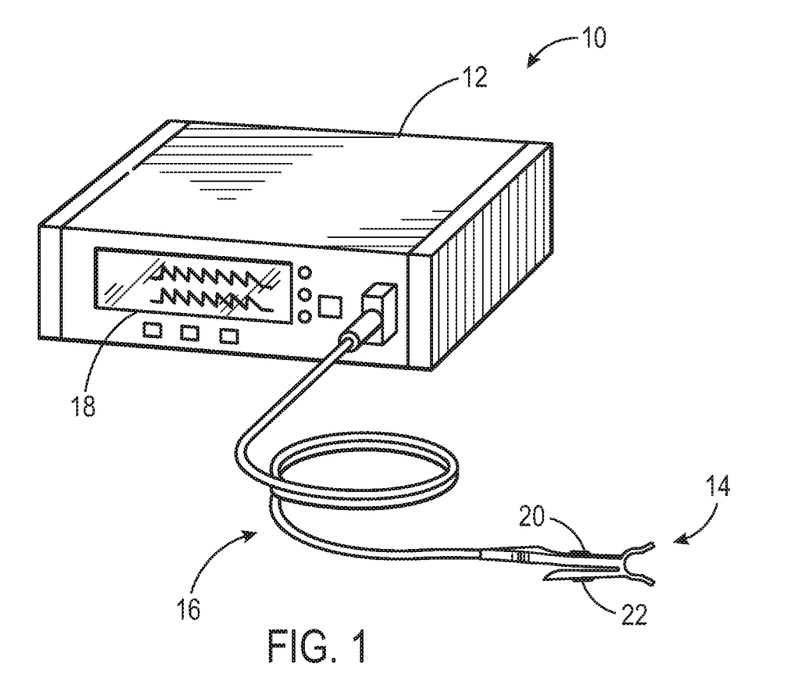
FIG. 1 is a perspective view of a non-invasive medical sensor system, in accordance with an embodiment.

With the foregoing in mind, FIG. 1 illustrates a perspective view of an embodiment of a non-invasive medical sensor system 10 involving an electronic patient monitor 12 and a medical sensor 14. Although the embodiment of the system 10 illustrated in FIG. 1 relates to pulse oximetry, the system 10 may be configured to obtain a variety of physiological measurements. For example, the system 10 may, additionally or alternatively, measure water fraction of tissue or perform other non-invasive medical monitoring techniques.

The patient monitor 12 may exchange signals with the medical sensor 14 via a communication cable 16. The patient monitor 12 may include a display 18, a memory, and various monitoring and control features. In certain embodiments, the patient monitor 12 may include a processor that may determine a physiological parameter of a patient based on these signals obtained from the medical sensor 14. Indeed, in the presently illustrated embodiment of the system 10, the medical sensor 14 is a pulse oximetry sensor that may non-invasively obtain pulse oximetry data from a patient. In other embodiments, the medical sensor 14 may represent any other suitable non-invasive optical sensor.

The medical sensor 14 may attach to pulsatile patient tissue (e.g., a patient's finger, ear, forehead, or toe). In the illustrated embodiment, the medical sensor 14 is configured to attach to a finger. An emitter 20 and a detector 22 may operate to generate non-invasive pulse oximetry data for use by the patient monitor 12. In particular, the emitter 20 may transmit light at certain wavelengths into the tissue and the detector 22 may receive the light after it has passed through or is reflected by the tissue. The amount of light and/or certain characteristics of light waves passing through or reflected by the tissue may vary in accordance with changing amounts of blood contingents in the tissue, as well as related light absorption and/or scattering.

The emitter 20 may emit light from two or more light emitting diodes (LEDs) or other suitable light sources into the pulsatile tissue. The light that is reflected or transmitted through the tissue may be detected using the detector 22, which may be a photodetector (e.g., a photodiode), once the light has passed through or has been reflected by the pulsatile tissue. When the detector 22 detects this light, the detector 22 may generate a photocurrent proportional to the amount of detected light, which may be transmitted through the cable 16 to the patient monitor 12. As described in greater detail below, the patient monitor 12 may convert the photocurrent from the detector 22 into a voltage signal that may be analyzed to determine certain physiological characteristics of the patient.

Figure 2:
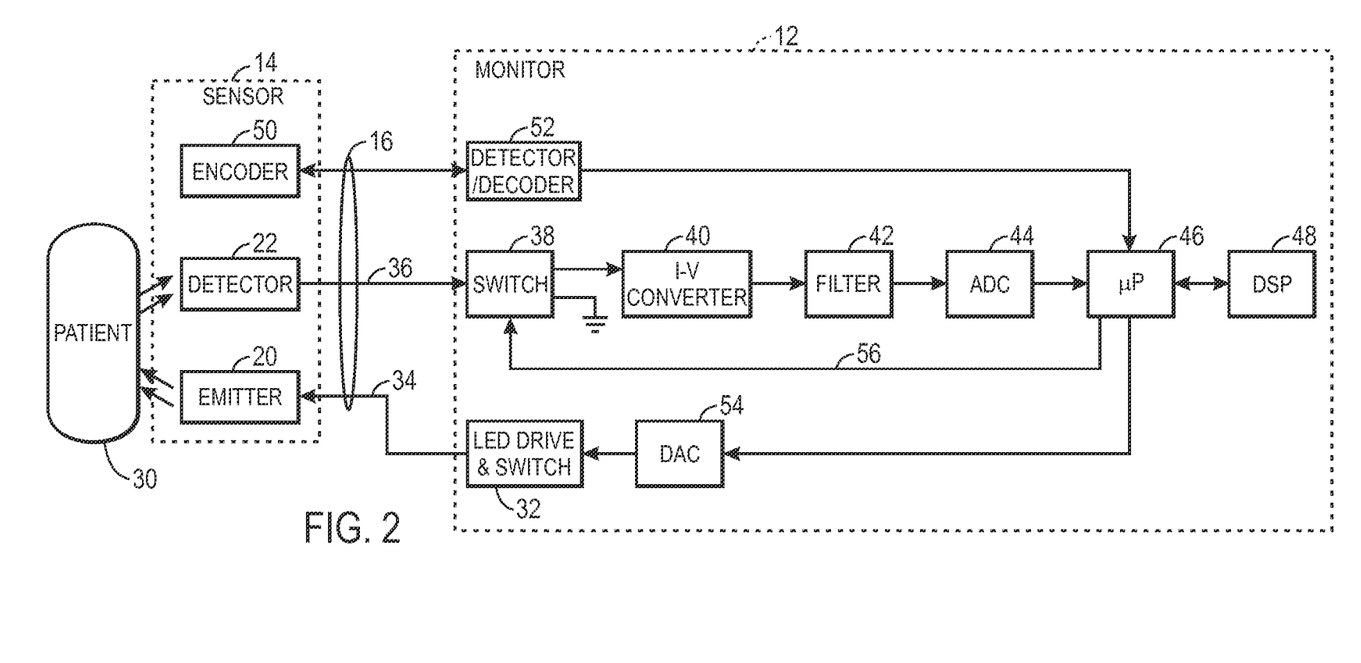
FIG. 2 is a block diagram of the medical sensor system of FIG. 1, in accordance with an embodiment.

As illustrated in FIG. 2, which describes the operation of the medical sensor system 10 in greater detail, the emitter 20 may emit light into a patient 30, which may be reflected by or transmitted through a patient 30 and detected by the detector 22. An LED drive and/or switch 32 may generate LED driving signals (e.g., LED current signals 34) to cause the LEDs of the emitter 20 to become excited and emit the light into the patient 30. In certain embodiments, the LED current signals 34 may include red wavelengths of between approximately 600-700 nm and/or infrared wavelengths of between approximately 800-1000 nm. In some embodiments, the LEDs of the emitter 20 may emit three or more different wavelengths of light. Such wavelengths may include a red wavelength of between approximately 620-700 nm (e.g., 660 nm), a far red wavelength of between approximately 690-770 nm (e.g., 730 nm), and an infrared wavelength of between approximately 860-940 nm (e.g., 900 nm). Other wavelengths may include, for example, wavelengths of between approximately 500-600 nm and/or 1000-1100 nm.

The detector 22 may detect a portion of the emitted light that passes through the tissue of the patient 30. In response to the light, the detector 22 may generate a photocurrent signal 36 that varies depending on the amount in wavelength of light emitted by the emitter 20 and the various physiological characteristics of the patient 30. As the LED current signals 34 vary to cause the emitter 20 to emit light or to stop emitting light, however, capacitive and/or inductive coupling between the LED current signals 34 and the photocurrent signal 36 may generate interference in the form of a transient current on the photocurrent signal 36. The magnitude of the transient current may depend on a variety of factors, such as the length of the cable 16, the amount and manner of shielding of the cable 16, the magnitude or amplitude of the LED current signals 34, and/or the manufacturer of the cable 16, and so forth. Since different cables 16 may have different capacitances and/or inductances, using different cables 16 may result in varying amounts of transient current arising in the photocurrent signal 36.

When the photocurrent signal 36 is received by the monitor 12, a switch 38 may provide the photocurrent signal 36 to a current-to-voltage (I-V) converter 40 or may discharge the photocurrent signal 36 to ground. When a transient current is not expected on the photocurrent signal 36, the switch 38 may provide the photocurrent signal 36 to the I-V converter 40. However, when the photocurrent signal 36 is expected to include the transient current, the switch 38 may discharge the transient current by coupling the photocurrent signal 36 to ground. After the transient current has been discharged, the switch 38 may provide the photocurrent signal 36 to the I-V converter 40.

The I-V converter 40 may convert the photocurrent signal 36 from the detector 22 into an output voltage signal. A DC component of the output voltage signal may be filtered out of the output voltage signal by a filter 42, such as a high pass (HP) filter or a band pass filter (BPF), and an analog-to-digital converter (ADC) 44 may digitize the resulting signal. In some embodiments, the filter 42 may be a low pass filter (LPF). A microprocessor 46, which may be a microcontroller (e.g., a PIC microcontroller), may receive the digitized signal and perform certain processing operations based on the digitized signal. In some embodiments, the microprocessor 46 may transfer certain data to another microprocessor, such as a digital signal processor (DSP) 48, which may determine certain physiological parameters of the patient 30.

In certain embodiments, the medical sensor 14 may also include an encoder 50 that may provide signals indicative of the wavelength of one or more light sources of the emitter 20, which may allow for selection of appropriate calibration coefficients for calculating a physical parameter such as blood oxygen saturation. The encoder 50 may, for instance, be a coded resistor, EEPROM or other coding devices (such as a capacitor, inductor, PROM, RFID, parallel resident currents, or a colorimetric indicator) that may provide a signal to the microprocessor 46 related to the characteristics of the medical sensor 14 to enable the microprocessor 46 to determine the appropriate calibration characteristics of the medical sensor 14. Further, the encoder 50 may include encryption coding that prevents a disposable part of the medical sensor 14 from being recognized by a microprocessor 46 unable to decode the encryption. For example, a detector/decoder 52 may be required to translate information from the encoder 50 before it can be properly handled by the processor 46. In some embodiments, the encoder 50 and/or the detector/decoder 52 may not be present.

The microprocessor 46 may control the LED drive and/or switch 32 as well as the switch 38. To control the LED drive and/or switch 32, the microprocessor 46 may transmit a digital control signal to a digital-to-analog converter (DAC) 54, which may convert the digital control signal to an analog control signal and provide the analog control signal to the LED drive and/or switch 32. Additionally, the microprocessor 46 may control the switch 38 via a control signal 56 based on when interference in the form of a transient current is expected to occur in the photocurrent signal 36. Since the microprocessor 46 may expect the transient current to occur when the LED current signals 34 rapidly increase or decrease, such as when the emitter 20 is switched on or off, the microprocessor 46 may control the switch 38 so that the photocurrent signal 36 is briefly discharged to ground every time the LED current signals 34 undergo a rapid change.

The LED drive and/or switch 32 may produce certain patterns of LED currents 34 to drive the emitter 20. For example, as illustrated in a timing diagram 70 of FIG. 3, the LED current 34 may include a component to drive a red wavelength LED, as represented by a curve 72, and may include a component to drive an infrared (IR) wavelength LED, as represented by a curve 74. In certain embodiments, currents represented by the curves 72 and 74 may be of opposite polarities (e.g., when the LED current signals 34 flow in a positive direction, red wavelength LEDs may emit light, and when the LED current signals 34 flow in a negative direction, IR wavelength LEDs may emit light). Light from the LEDs of the emitter 20 may pass through the patient 30 to be detected by the detector 22, which may generate the photocurrent signal 36. One representation of such a photocurrent signal 36 appears as a curve 76.

Figure 3:
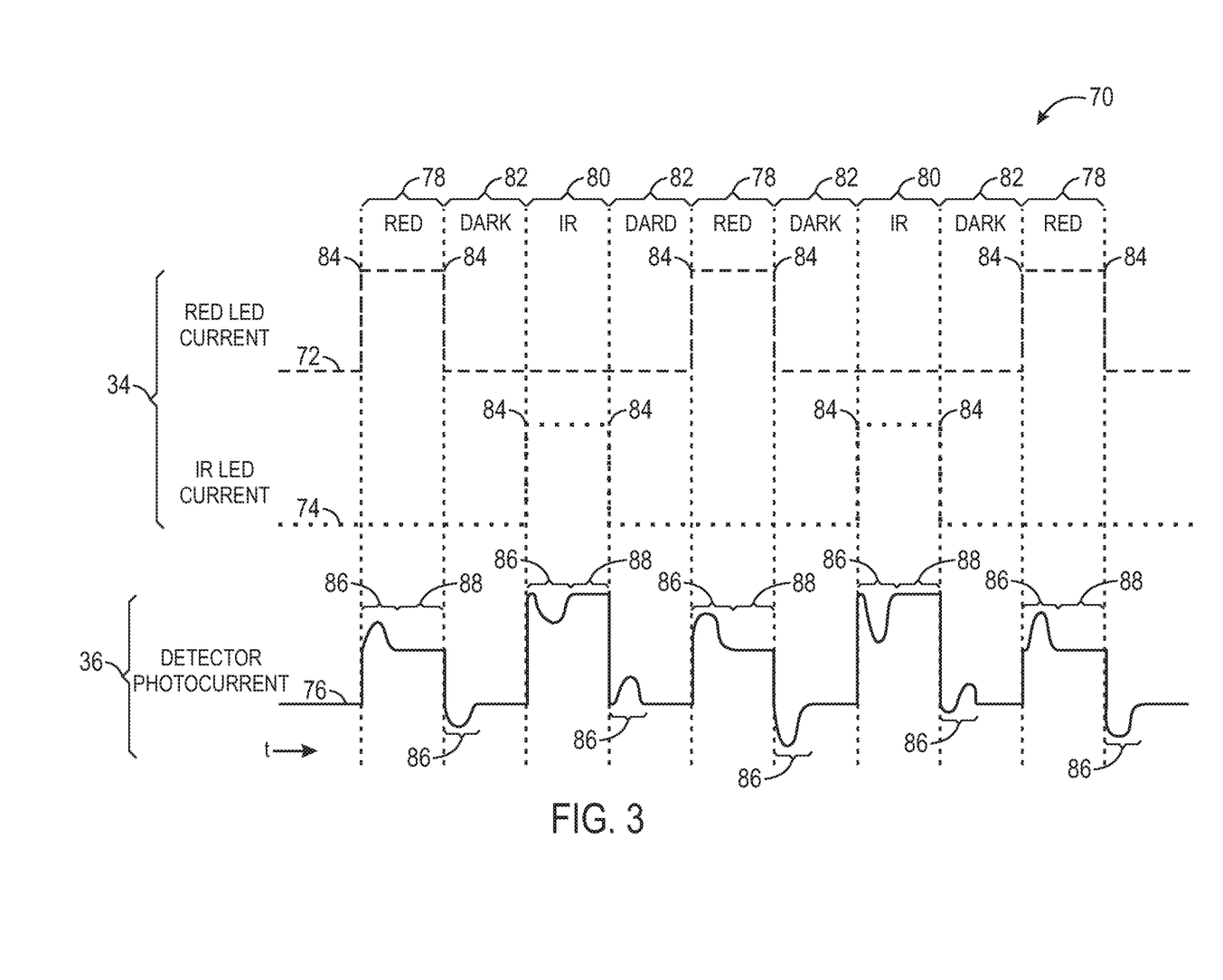
FIG. 3 is a timing diagram representing emitter and detector signals employed by the sensor system of FIG. 1, in accordance with an embodiment.

Different periods of operation may be defined depending upon the type of light being emitted by the emitter 20. During red periods 78, as indicated by the curve 72, the LED current signals 34 activate red wavelength LEDs. Similarly, during infrared (IR) periods 80, as indicated by the curve 74, the LED current signals 34 activate IR wavelength LEDs. The red period 78 and the IR period 80 may be punctuated by dark periods 82, during which the emitter 20 may not emit any light. When techniques of the present disclosure are employed, the red periods 78 and/or the IR periods 80 may be relatively short (e.g., less than 200 μs, less than 100 μs, and/or less than 50 μs).

During the various periods 78, 80, and 82, the detector 22 may detect varying amounts of light passing through the patient 30. As represented by the curve 76, the detector photocurrent signal 36 generally may increase during the red period 78 and the IR periods 80 due to light passing through the patient 30. Additionally, when the LED current signals 34 change rapidly to activate or deactivate the LEDs of the emitter 20, as may occur at edges 84 of the curves 72 and 74, a transient current 86 may arise in the photocurrent signal 36, interfering with the photocurrent signal 36. If the switch 38 does not couple the photocurrent signal 36 to ground when the transient current 86 appears in the photocurrent signal 36, the transient current 86 may remain until fully discharged by the I-V converter 40. If the switch 38 does couple the photocurrent signal 36 to ground when the transient current 86 appears in the photocurrent signal 36, the transient current may discharge more quickly. Once the transient current 86 has been discharged, a signal of interest 88 may remain.

Figure 4:
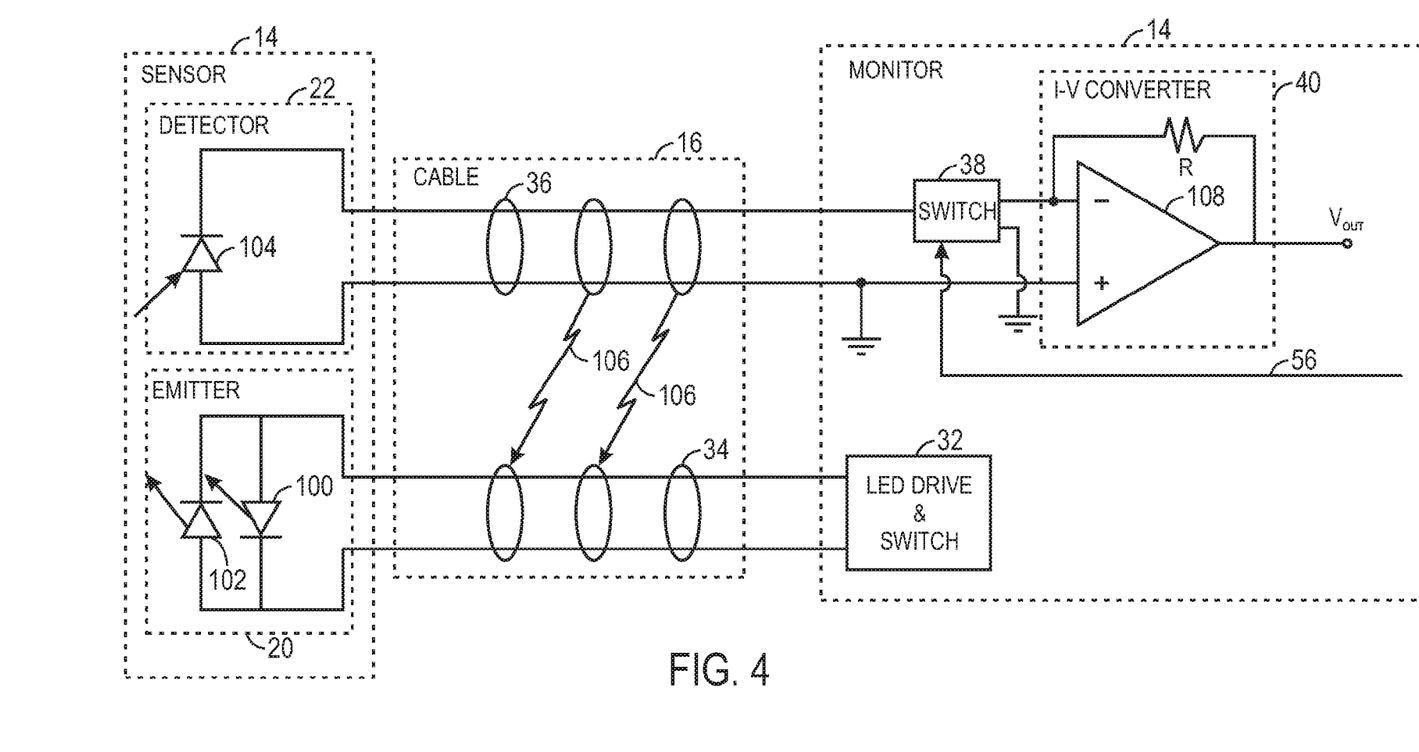
FIG. 4 is a schematic circuit diagram depicting elements of the medical sensor system of FIG. 1 in greater detail, in accordance with an embodiment.

A more detailed view of certain elements of one embodiment of the medical sensor system 10 appears in FIG. 4. In particular, the LED drive and/or switch 32 may generate the LED current signals 34 to drive red LEDs 100 and infrared (IR) LEDs 102 with currents of varying polarities. In other embodiments, however, any suitable number of LED current signals 34 may be supplied to any suitable number of LEDs of various other wavelengths, as mentioned above. A photodiode 104 of the detector 22 of the medical sensor 14 may generate the photocurrent signal 36 in response to detected light. Both the photocurrent signal 36 and the LED current signals 34 may both traverse the cable 16.

Since, as mentioned above, the cable 16 may be of varying length and/or manufactured by various vendors, the cable 16 may also have varying capacitive and/or inductive qualities. When the LED current signals 34 pass through the cable 16, capacitive and/or inductive coupling 106 may occur between the LED current signals 34 and the photocurrent signal 36. As mentioned above, this coupling 106 may cause transient current 86 to arise on the photocurrent signal 36. Because the transient current 86 of the photocurrent signal 36 could dissipate slowly if the photocurrent signal 36 were supplied directly to the I-V converter 40, the control signal 56 from the microprocessor 46 may cause the switch 38 to discharge the photocurrent signal 36 to ground when the transient current 86 is expected to occur. After the transient current has been discharged, the switch 38 may couple the photocurrent signal 36 to the I-V converter 40.

The I-V converter 40 may convert the photocurrent signal 36 to the output voltage signal as a transimpedance amplifier. As such, the I-V converter 40 include an operational amplifier (op amp) 108 with negative feedback to an inverting (−) junction of the op amp 108 separated by a transimpedance R. In general, the higher the transimpedance R, the higher the gain and the higher the signal-to-noise ratio (SNR) with respect to thermal Johnson noise. If the transient current 86 were not discharged to ground by the switch 38, a higher transimpedance R of the I-V converter 40 would discharge the transient current 86 more slowly.

Figure 5:
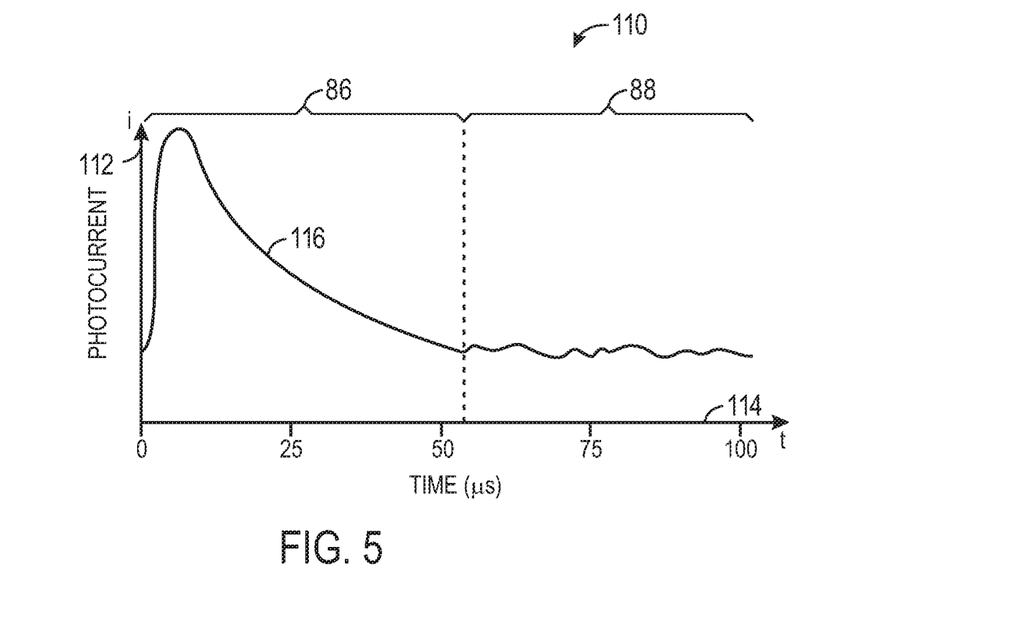
FIG. 5 is a plot modeling a photocurrent when a transient current is discharged using a current-to-voltage converter.

As noted above, the switch 38 may couple the photocurrent signal 36 to ground when transient current is expected to occur in the photocurrent signal 36. If the switch 38 did not couple the photocurrent signal 36 to ground, the transient current 86 could make up a substantial component of the photocurrent signal 36 during the red periods 78 or IR periods 80. For example, FIG. 5 depicts a plot 110 modeling the photocurrent signal 36 (ordinate 112) over time in units of microseconds (μs) (abscissa 114) when the switch 38 only provides the photocurrent signal 36 to the I-V converter 40 during a red period 78 or an IR period 80. A curve 116 represents the photocurrent signal 36, beginning when the emitter 20 starts emitting light during the red period 78 or the IR period 80. As such, the curve 116 spikes near the start of the plot 110, as capacitive and/or inductive coupling 106 between the LED current signals 34 and the photocurrent signal 36 produce transient current 86.

If the switch 38 did not discharge the transient current 86, the I-V converter 40 may slowly discharge the transient current 86 (e.g., over a period of approximately 50 μs, depending on the transimpedance R of the I-V converter 40 and/or the capacitive and/or inductive characteristics of the cable 16). After the photocurrent signal 36 has stabilized, the signal of interest 88 may be used to determine a physiological parameter of the patient 30.

To avoid such a relatively long discharge time without compromising the gain or the SNR of the I-V converter 40, the switch 38 may instead couple the photocurrent signal 36 to ground to discharge the transient current 86 before coupling the photocurrent signal 36 to the I-V converter 40. For example, as illustrated by a flowchart 120 of FIG. 6, the microprocessor 46 may cause the switch 38 to couple the photocurrent signal 36 to ground when a transient current 86 is expected. The flowchart 120 may begin when the detector 22 may generate the photocurrent signal 36, which may be received by the patient monitor 12 (block 124). In certain situations, through capacitive and/or inductive coupling 106 with LED current signals 34, a transient current 86 may arise in the photocurrent signal 36.

Figure 6:
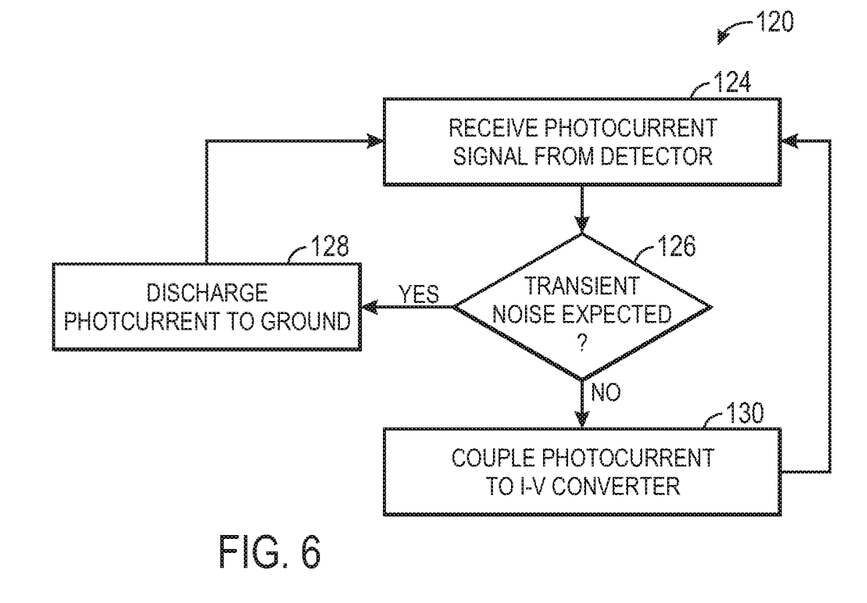
FIG. 6 is a flowchart describing an embodiment of a method for discharging the transient current when the transient current is expected to occur.

Accordingly, if the microprocessor 46 expects that the transient current 86 may be present in the photocurrent signal 36 (decision block 126), the microprocessor 46 may generate a control signal 56 to cause the switch 38 to couple the photocurrent signal 36 to ground for a certain period of time (block 128). Such a period of time may be selected to ensure that the transient current 86 is fully discharged. For instance, in one embodiment, the switch 38 may couple the photocurrent signal 36 to ground for less than 50 μs, less than 30 μs, and/or less than 10 μs. When the microprocessor 46 is not expecting the transient current 86 to be present in the photocurrent signal 36 (decision block 126), the microprocessor 46 may generate a control signal 56 to cause the switch 38 to couple to the I-V converter 40 (block 130).

Figure 7:
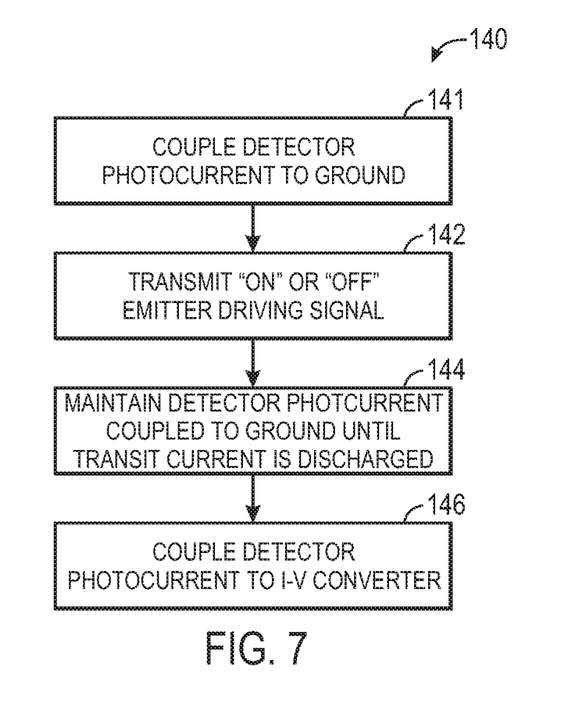
FIG. 7 is a flowchart describing an embodiment of a method for discharging the transient current when the emitter driving signals are switched on or off.

The microprocessor 46 may generally expect the transient current 86 to occur on the photocurrent signal 36 when the microprocessor 46 instructs the LED drive and/or switch 32 to vary the LED current signals 34, which may switch on or off an LED of the emitter 20. One embodiment of a method for controlling the switch 38 in such a manner is illustrated in FIG. 7. In particular, FIG. 7 is a flowchart 140 describing an embodiment of a method for controlling the switch 38 based on changes to the LED current signals 34. The flowchart 140 may begin just before or concurrently when the LED 100 or the LED 102 start emitting light or stop emitting light. In particular, the microprocessor 46 may generate a control signal 56 to cause the switch 38 to couple the photocurrent signal 36 to ground for a certain period of time (block 141) just before or while causing the LED current signals 34 to switch an LED 100 or 102 on or off to begin or end a red period 78 or an IR period 80 (block 142). The switch 38 may couple the photocurrent signal 36 to ground for a certain period of time after the LEDs 100 or 102 have been switched on or off, to discharge the transient current 86 that may be due to capacitive and/or inductive coupling 106 (block 144). Once the transient current 86 has been discharged, the microprocessor 46 may generate another control signal 56 to cause the switch 38 to couple the photocurrent signal 36 to the I-V converter 40 (block 146).

Because the switch 38 may couple the photocurrent signal 36 to ground, rather than to the I-V converter 40, the transient current 86 may discharge relatively rapidly. Moreover, the discharge time of the transient current 86 largely may be independent of the gain and/or SNR of the I-V converter 40 and/or the characteristics of the cable 16. For example, the transimpedance R of the I-V converter 40 may be greater than 100 kΩ (e.g., 1MΩ or greater). The cable 16 may be vary in length and have any of a variety of capacitive and/or inductive characteristics, For example, the lines for the LED current signals 34 and the photocurrent signal 36 may be approximately 23 pF/foot (e.g., 230 pF for a 10 foot cable 16). Stray capacitance may exist across shielding material surrounding the lines for the LED current signals 34 and the photocurrent signal 36. Differential capacitances between the lines for the LED current signals 34 and the photocurrent signal 36 may vary widely but is expected to be a few pF (e.g., between approximately 1 to 10 pF; e.g., 3 pF).

Figure 8:
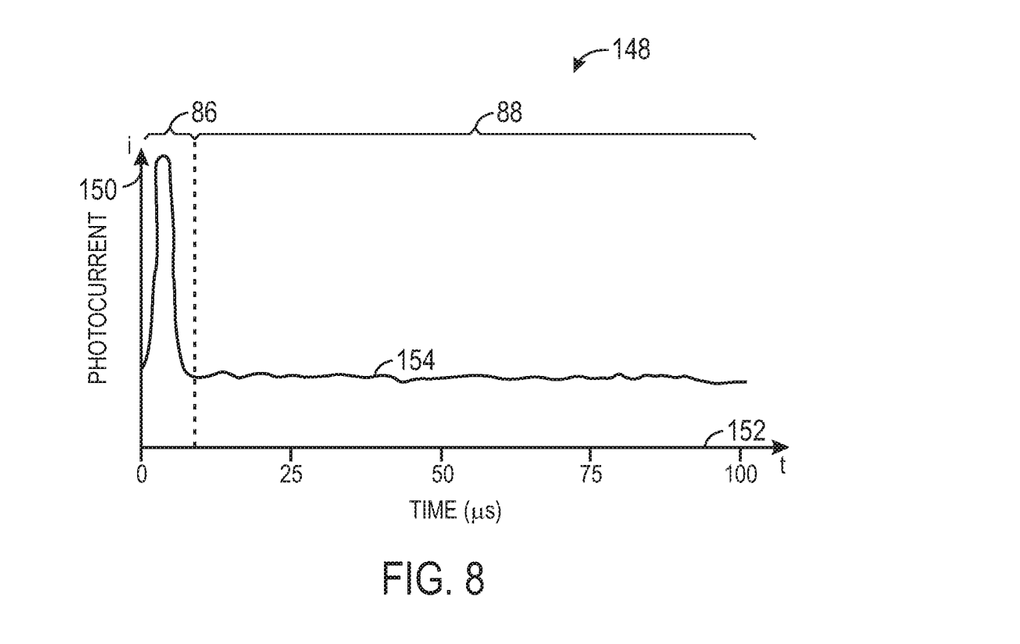
FIG. 8 is a plot modeling a photocurrent when the transient current is discharged before being coupled to a current-to-voltage converter, in accordance with an embodiment.

Such a rapid discharge time due to employing the techniques described in FIGS. 6 and/or 7 is modeled by a plot 148 of FIG. 8. The plot 148 compares the photocurrent signal 36 (ordinate 150) and over time in units of μs (abscissa 152) during a red period 78 or an IR period 80. At the start of the red period 78 or the IR period 80, a curve 154 representing the photocurrent signal 36 is shown to spike due to transient current 86. However, because the transient current 86 is discharged to ground rather than discharged by the transimpedance R of the I-V converter, the transient current 86 is fully discharged within a short period of time. In addition, the amplitude of the transient current 86 may be greatly reduced, since the transient current 86 is being directly shunted to ground rather than being amplified by the transimpedance R. Here, the discharge time is shown as approximately 10 μs, but the discharge time may be shorter or longer. As a result, the signal of interest 88 may be obtained more quickly.

Employing the present techniques, the transimpedance R of the I-V converter 40 may be increased, improving the sensitivity and the SNR of the I-V converter 40. Moreover, because the signal of interest 88 is obtained more quickly as a result of the quicker discharge times, the LED current signals 34 may drive the emitter 20 with shorter pulse times (e.g., pulses of less than 200 μs, less than 100 μs, and/or less than 50 μs, and so forth depending on the discharge time). Cables 16 of varying capacitance and/or lengths also may be employed without significant changes in the amount of the signal of interest 88 of the photocurrent signal 36, since different amounts of transient current 86 may all discharge relatively quickly to ground.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. An electronic patient monitor comprising:
   driving circuitry configured to generate an emitter control signal to cause an emitter of a medical sensor to emit light into a patient;
   an amplifier configured to receive a detector signal generated when a detector of the medical sensor detects emitted light that passes through the patient; and
   transient current discharge circuitry configured to discharge a transient current from the detector signal due to inductive coupling or capacitive coupling, or a combination thereof, of the emitter control signal with the detector signal, such that the transient current is at least partially discharged from the detector signal when the detector signal is received by the amplifier.

2. The patient monitor of claim 1, wherein the transient current discharge circuitry comprises a switch configured to couple the detector signal to ground when the transient current occurs.

3. The patient monitor of claim 2, wherein the switch is configured to couple the detector signal to ground for a period of time that begins before or when the emitter control signal is generated.

4. The patient monitor of claim 3, wherein the period of time is less than 30 microseconds.

5. The patient monitor of claim 1, comprising processing circuitry configured to control the driving circuitry and the transient current discharge circuitry, wherein the processing circuitry is configured to cause the transient current discharge circuitry to discharge the transient current from the detector signal when the processing circuitry causes the driving circuitry to generate the emitter control signal.

6. The patient monitor of claim 1, wherein the emitter control signal is configured to cause the emitter to emit light for less than 200 microseconds.

7. The patient monitor of claim 1, wherein the emitter control signal is configured to cause the emitter to emit light for 50 microseconds or less.

8. The patient monitor of claim 1, wherein the detector signal is a current signal and wherein the amplifier comprises a transimpedance amplifier configured to convert the detector signal into a voltage signal via a transimpedance, wherein the transimpedance, in the absence of the transient current discharge circuitry, would not discharge the transient current before the emitter control signals varied to cause the emitter of the medical sensor to stop emitting light into the patient.

9. A method comprising:
   providing an emitter control signal to an emitter to cause the emitter to emit light into a patient using emitter control circuitry; and
   receiving into signal receiving circuitry a detector signal generated by a detector when the detector senses emitted light that passes through the patient, wherein:
   when transient current is expected in the detector signal, the signal receiving circuitry couples the detector signal to ground to discharge the transient current; and
   when the transient current is not expected in the detector signal, the signal receiving circuitry couples the detector signal to an amplifier.

10. The method of claim 9, wherein the transient current is expected in the detector signal immediately after the emitter control signal is provided to the emitter.

11. The method of claim 9, wherein the transient current is not expected in the detector signal after the detector signal has been coupled to ground for a period of time.

12. The method of claim 9, wherein the emitter control signal comprises a driving current and the detector signal comprises a photocurrent, wherein the transient current in the detector signal is due to capacitive coupling or inductive coupling, or a combination thereof, of the photocurrent with the driving current.

13. The method of claim 12, wherein the signal receiving circuitry couples the detector signal to an amplifier when the transient current is not expected in the detector signal, wherein the amplifier comprises a current-to-voltage converter.

14. The method of claim 9, comprising determining when the transient current is expected in the detector signal using a processor and controlling the signal receiving circuitry to either couple the detector signal to ground or to the amplifier using a signal generated by the processor, wherein the emitter control signal is provided to the emitter using the emitter control circuitry under the control of the processor, wherein the transient current is determined to be expected when the processor causes the emitter control circuitry to provide the emitter control signal.

15. A system comprising:
   a medical sensor capable of emitting light into a patient in response to an emitter driving current, detecting a portion of the emitted light that passes through the patient, and generating a photocurrent based on the detected light; and
   a patient monitor capable of generating the emitter driving current, receiving the photocurrent, and discharging transient current in the photocurrent before converting the photocurrent to a voltage.

16. The system of claim 15, comprising a patient cable capable of transmitting the emitter driving current to the medical sensor from the patient monitor and the photocurrent to the patient monitor from the medical sensor, wherein a differential capacitance between components capable of transmitting the emitter driving current and the photocurrent exceeds 3 pF.

17. The system of claim 15, wherein the patient monitor is capable of coupling the photocurrent to ground for a period of time immediately after the medical sensor begins emitting light into the patient in response to the emitter driving current.

18. The system of claim 15, wherein the patient monitor is capable of coupling the photocurrent to a current-to-voltage converter to convert the photocurrent to the voltage after the transient current in the photocurrent has been discharged.

19. The system of claim 15, wherein the patient monitor is capable of converting the photocurrent to the voltage using a transimpedance amplifier having a transimpedance that exceeds 100 kΩ.

20. The system of claim 15, wherein the patient monitor is capable of converting the photocurrent to the voltage using a transimpedance amplifier having a transimpedance of at least 100 kΩ.

* * * * *